(12) United States Patent
Canham

(10) Patent No.: US 6,322,895 B1
(45) Date of Patent: Nov. 27, 2001

(54) BIOMATERIAL

(75) Inventor: Leigh T Canham, Malvern (GB)

(73) Assignee: QinetiQ Limited, London (GB)

( * ) Notice: Subject to any disclaimer, the term of this patent is extended or adjusted under 35 U.S.C. 154(b) by 0 days.

(21) Appl. No.: 09/000,258

(22) PCT Filed: Aug. 1, 1996

(86) PCT No.: PCT/GB96/01863

§ 371 Date: Jan. 30, 1998

§ 102(e) Date: Jan. 30, 1998

(87) PCT Pub. No.: WO97/06101

PCT Pub. Date: Feb. 20, 1997

(30) Foreign Application Priority Data

Aug. 3, 1995 (GB) .................................................. 9515956
Nov. 28, 1995 (GB) .................................................. 9524242
May 31, 1996 (GB) .................................................. 9611437

(51) Int. Cl.$^7$ ..................................................... B32B 9/00
(52) U.S. Cl. ............................ 428/450; 428/446; 427/58
(58) Field of Search .................................. 428/446, 450; 427/2.24, 2.27, 457, 58; 204/403

(56) References Cited

U.S. PATENT DOCUMENTS 4,569,743 * 2/1986 Bayer et al. ...................... 204/192.5
5,348,618 9/1994 Canham et al. .
5,358,600 * 10/1994 Canham .

FOREIGN PATENT DOCUMENTS

361218932A * 9/1986 (JP) .
405049691A * 3/1993 (JP) .
405337137A * 12/1993 (JP) .
6-169981 6/1994 (JP) .

OTHER PUBLICATIONS

Database WOP Week 8645 Derwent Publications Ltd., London, GB; AN 86–295840 XP002021586 & JP, A, 61 218 932 (Toko), Sep. 29, 1986 see abstract.

Database WPI Week 9429 Derwent Publications Ltd., London, GB; AN 94–237642 XO002021587 & JP,A,06 169 981 (Erusoru), Jun. 21, 1994 see abstract.

* cited by examiner

Primary Examiner—Deborah Jones
Assistant Examiner—Stephen Stein
(74) Attorney, Agent, or Firm—Nixon & Vanderhye

(57) ABSTRACT

Bioactive silicon comprising a porous form of silicon which when in vivo elicits a specific biological response that results in the formation of a bond between living tissue and the silicon. The deposition of apatite provides an indication that the porous silicon is bioactive and therefore biocompatible. Bioactive silicon may be used in the fabrication of biosensors for in vitro or in vivo applications.

6 Claims, 7 Drawing Sheets

BIOMATERIAL

This is a 35 U.S.C. §371 of PCT/GB96/01863, filed Aug. 1, 1996.

The present invention relates to biomaterials.

A "biomaterial" is a non-living material used in a medical device which is intended to interact with biological systems. Such materials may be relatively "bioinert", "biocompatible", "bioactive" or "uresorbable", depending on their biological response in vivo.

Bioactive materials are a class of materials each of which when in vivo elicits a specific biological response that results in the formation of a bond between living tissue and that material. Bioactive materials are also referred to as surface reactive biomaterials. Biomaterials may be defined as materials suitable for implantation into a living organism. L. L. Hench has reviewed biomaterials in a scientific paper published in Science, Volume 208, May 1980, pages 826–831. Biomaterials which are relatively inert may cause interfacial problems when implanted and so considerable research activity has been directed towards developing materials which are bioactive in order to improve the biomaterial-tissue interface.

Known bioactive materials include hydroxyapatite (HA), some glasses and some glass ceramics. Both bioactive glasses and bioactive glass ceramics form a biologically active layer of hydroxycarbonateapatite (HCA) when implanted. This layer is equivalent chemically and structurally to the mineral phase in bone and is responsible for the interfacial bonding between bone and the bioactive material. The properties of these bioactive materials are described by L. L. Hench in the Journal of the American Ceramic Society, Volume 74 Number 7, 1991, pages 1487–1510. The scientific literature on bioactive materials often uses the terms HA and HCA on an interchangeable basis. In this patent specification, the materials HA and HCA are collectively referred to as apatite.

Li et al. have reported the deposition of apatite on silica gel in the Journal of Biomedical Materials Research, Volume 28, 1994, pages 7–15. They suggest that a certain density of silanol (SiOH) groups is necessary to trigger the heterogeneous nucleation of hydroxyapatite. An apatite layer did not develop on the surface of a silica glass sample and this is attributed to the lower density of surface silanol groups compared with silica gel.

Thick films of apatite have previously been deposited on silicon single crystal wafers by placing the wafers in close proximity to a plate of apatite and wollastonite-containing glass dipped into a physiological solution at 36° C., as described by Wang et al. in the Journal of Materials Science: Materials In Medicine, Volume 6, 1995, pages 94–104. A physiological solution, also known as a simulated body fluid (SBF), is a solution containing ion concentrations similar to those found in the human body and is widely used to mimic the behavior of the body in vitro tests of bioactivity. Wang et al. reported the growth of apatite on (111) Si wafers but reported that "hardly any" apatite could be grown on (100) Si wafers. The silicon wafer itself is not bioactive. Wang et al. state that "Si does not play any special role in the growth of (the) apatite film except that Si atoms on the substrate can bond strongly with oxygen atoms in apatite nuclei to form interfaces with low energy". The presence of the apatite and wollastonite containing glass is required to induce the deposition of the apatite. Indeed, this so-called "biomimetic process" whereby a bioactive material is used to treat another material has been shown to induce apatite growth on a wide variety of bioinert materials, as reported by Y. Abe et al. in the Journal of Materials Science: Materials In Medicine, Volume 1, 1990, pages 233 to 238.

There is a long felt want for the ability to use silicon based integrated circuits within the human body both for diagnostic and therapeutic purposes. Silicon has been reported to exhibit a poor biocompatibility in blood, Kanda et al. in Electronics Letters, Volume 17, Number 16, 1981, pages 558 and 559, and in order to protect integrated circuits from damage in biological environments encapsulation by a suitable material is currently required. Medical applications for silicon based sensors are described in a paper by Engels et al. in the Journal of Physics E: Sci. Instrum., Volume 16, 1983, pages 987 to 994.

The present invention provides bioactive silicon characterized in that the silicon is at least partly crystalline.

Bioactive silicon provides the advantage over other bioactive materials that it is compatible with silicon based integrated circuit technology. It has the advantage over non-bioactive silicon that it exhibits a greater degree of biocompatibility. In addition, bioactive silicon may be used for forming a bond to bone or vascular tissue of a living animal. Bioactive silicon may provide a material suitable for use as a packaging material in miniaturised packaging applications.

The bioactive nature of the silicon may be demonstrated by the immersion of the material in a simulated body fluid held at a physiological temperature, such immersion producing a mineral deposit on the bioactive silicon. The mineral deposit may be apatite. The apatite deposit may be continuous over an area greater than $100\,\mu m^2$. The bioactive silicon may be at least partially porous silicon. The porous silicon may have a porosity greater than 4% and less than 70%.

Bulk crystalline silicon can be rendered porous by partial electrochemical dissolution in hydrofluoric acid based solutions, as described in U.S. Pat. No. 5,348,618. This etching process generates a silicon structure that retains the crystallinity and the crystallographic orientation of the original bulk material. The porous silicon thus formed is a form of crystalline silicon. At low levels of porosity, for example less than 20%, the electronic properties of the porous silicon resemble those of bulk crystalline silicon.

Porous silicon may be subdivided according to the nature of the porosity. Microporous silicon contains pores having a diameter less than 20 Å; mesoporous silicon contains pores having a diameter in the range 20 Å to 500 Å; and macroporous silicon contains pores having a diameter greater than 500 Å. The bioactive silicon may comprise porous silicon which is either microporous or mesoporous.

Silicon has never been judged a promising biomaterial, in contrast with numerous metals, ceramics and polymers, and has never been judged capable of exhibiting bioactive behavior. Indeed, no semiconductors have been reported to be bioactive. Silicon is at best reported to be relatively bioinert but generally exhibits poor biocompatibility. Despite the advances made in miniaturisation of integrated circuitry, silicon VLSI technology is still under development for invasive medical and biosensing applications, as described by K. D. Wise et al. in "VLSI in Medicine" edited by N. G. Einspruch et al., Academic Press, New York, 1989, Chapter 10 and M. Madou et al. in Appl. Biochem. Biotechn., Volume 41, 1993, pages 109–128.

The use of silicon structures for biological applications is known. International patent application PCT/US95/02752 having an International Publication Number WO 95/24472 describes a capsule having end faces formed from a perforated amorphous silicon structure, whose pores are large enough to allow desired molecular products through but which block the passage of larger immunological molecules, to provide immunological isolation of cells contained therein. No evidence as to the biocompatibility of the silicon structure is provided, and workers skilled in the field of biocompatible materials would expect that such a device would in vivo stimulate the production of fibrous tissue which would block the pores. It is known that when micromachined silicon structures are used as sensors for neural elements a layer of fibrous tissue forms between the silicon surfaces and the neural elements of interest, as reported by D. J. Edell et al. in IEEE Transactions on Biomedical Engineering, Volume 39, Number 6, 1992 page 635. Indeed the thickness and nature of any fibrous tissue layer formed is often used as one measure of biocompatibility, with a thinner layer containing little cell necrosis reflecting a higher degree of biocompatibility.

U.S. Pat. No. 5,225,374 describes the use of porous silicon as a substrate for a protein-lipid film which interacts with target species to produce an electrical current when exposed to target species in an in vitro solution. The porous silicon is oxidised to produce a hydrophilic surface and is chosen since the pores act as a conduit for an ion-current flow and the structure provides structural support for the lipid layer. The porous silicon is separated from the in vitro solution by the protein-lipid film and so the question of the bioactivity or biocompatibility of the porous silicon does not arise.

Porous silicon has been suggested as a substrate material for in vitro biosensors by M. Thust et al. in Meas. Sci. Technol, Volume 7 1996 pages 26–29. In the device structure described therein, the porous silicon is subjected to a thermal oxidation process to form a silicon dioxide layer on the exposed silicon surfaces of the pores. Since the porous silicon is partially thermally oxidised, the bioactivity or biocompatibility of the silicon is not of relevance since it is only the silicon dioxide which is exposed to test solutions. The porous silicon is effectively an inert host for enzyme solutions.

Microperforated silicon membranes have been described as being capable of supporting cell structures by E. Richter et al. in Journal of Materials Science: Materials in Medicine, Volume 7, 1996, pages 85–97, and by G. Fuhr et al. in Journal of Micromechanics and Microengineering, Volume 5, Number 2, 1995, pages 77–85. The silicon membranes described therein comprises silicon membranes of thickness 3 $\mu$m perforated by square pores of width 5 $\mu$m to 20 $\mu$m using a lithography process. Mouse embryo fibroblasts were able to grow on cleaned membranes but adherence of the cells was improved if the membranes were coated with polylysine. This paper is silent as to the bioactivity of the silicon membrane, and there is no mention of an apatite layer having been formed when exposed to the cell culture medium. Indeed, given the dimensions of the pores used, the structure is not likely to exhibit a significant degree of bioactivity. Furthermore, it is accepted by Fuhr et al. that there is still a need to find and develop cell-compatible materials with long term stability.

A.Offenhäusser et al. in Journal of Vacuum Science Technology A, Volume 13, Number 5, 1995, pages 2606–2612 describe techniques for achieving biocompatibility with silicon substrates by coating the substrate with an ultrathin polymer film. Similarly, R. S. Potember et al. in Proc. 16th Int. Conf. IEEE Engineering in Medicine and Biology Society, Volume 2, 1994, pages 842–843 describe the use of a synthetic peptide attached to a silicon surface to promote the development of rat neurons.

In a further aspect, the invention provides a bioactive silicon structure characterized in that the silicon is at least partly crystalline.

In a still further aspect, the invention provides an electronic device for operation within a living human or animal body, characterized in that the device includes bioactive silicon.

Bioactive silicon of the invention may be arranged as a protective covering for an electronic circuit as well as a means for attaching a device to bone or other tissue.

The electronic device may be a sensor device or a device for intelligent drug delivery or a prosthetic device.

In a still further aspect, the invention provides a method of making silicon bioactive wherein the method comprises making at least part of the silicon porous.

In another aspect, the invention provides a method of fabricating bioactive silicon, characterized in that the method comprises the step of depositing a layer of polycrystalline silicon.

In a yet further aspect, the invention provides biocompatible silicon characterized in that the silicon is at least partly crystalline.

In a still further aspect, the invention provides resorbable silicon.

In another aspect, the invention provides a method of accelerating or retarding the rate of deposition of a mineral deposit on silicon in a physiological electrolyte wherein the method comprises the application of an electrical bias to the silicon.

The silicon may be porous silicon.

In a further aspect, the invention provides bioactive material characterised in that the bioactivity of the material is controllable by the application of an electrical bias to the material.

Conventional bioactive ceramics are electrically insulating and therefore preclude their use in electrochemical applications. Where the electrical stimulation of tissue growth has been studied previously, it has often been difficult to distinguish the direct effects of electric fields from those associated with an altered body chemistry near implanted "bioinert" electrodes.

In a still further aspect, the invention provides a composite structure comprising bioactive silicon region and a mineral deposit thereon characterized in that the silicon region comprises silicon which is at least partly crystalline.

A possible application of the invention is as a substrate for performing bioassays. It is desirable to be able to perform certain tests on pharmaceutical compounds without resorting to performing tests on living animals. There has therefore been a considerable amount of research activity devoted to developing in vitro tests in which cell lines are supported on a substrate and the effects of pharmaceutical compounds on the cell lines monitored. A composite structure of silicon and apatite might provide a suitable substrate for such tests.

In a further aspect, the invention provides a method of fabricating a biosensor, characterized in that the method includes the step of forming a composite structure of bioactive silicon and a mineral deposit thereon.

The invention further provides a biosensor for testing the pharmacological activity of compounds including a silicon substrate, characterized in that at least part of the silicon substrate is comprised of bioactive silicon.

BRIEF DESCRIPTION OF THE DRAWINGS

In order that the invention may be more fully understood, embodiments thereof will now be described, by way of example only, with reference to the accompanying drawings, in which.

DETAILED DESCRIPTION OF THE INVENTION

Figure 1:
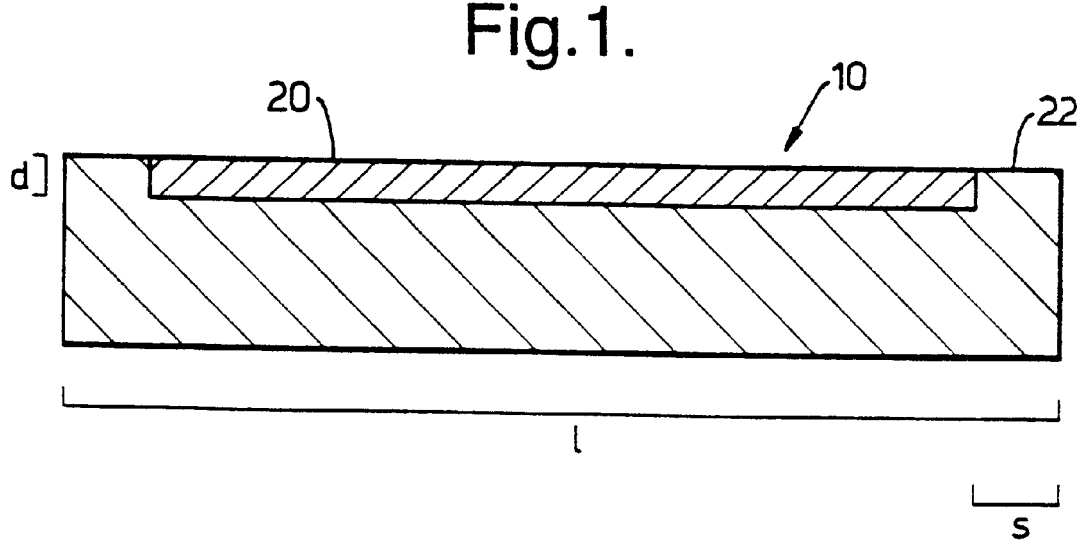
FIG. 1 is a schematic sectional diagram of a bioactive silicon wafer.

Referring to FIG. 1 there is shown a section of a bioactive silicon wafer, indicated generally by 10. The silicon wafer 10 comprises a porous silicon region 20 and a non-porous bulk silicon region 22. The porous region 20 has a thickness d of 13.7 µm and an average porosity of 18%. The silicon wafer 10 has a diameter l of three inches or 75 mm. The porous region 20 has a surface area per unit mass of material of 67 $m^2g^{-1}$. This was measured using a BET gas analysis technique, as described in "Adsorption, Surface Area and Porosity" by S. J. Gregg and K. S. W. Sing, 2nd edition, Academic Press, 1982.

The wafer 10 was fabricated by the anodisation of a heavily arsenic doped Czochralski-grown (CZ) n-type (100) silicon wafer having an initial resistivity of 0.012 Ωcm. The anodisation was carried out in an electrochemical cell, as described in U.S. Pat. No. 5,348,618, containing an electrolyte of 50 wt % aqueous HF. The wafer was anodised using an anodisation current density of 100 $mAcm^{-2}$ for one minute. The wafer was held in place in the electrochemical cell by a synthetic rubber washer around the outside of the wafer. Consequently, an outer ring of the wafer remained unanodised after the anodisation process. This outer unanodised. ring is shown in FIG. 1 as a non-porous bulk silicon region 22. The unanodised ring has a width s of 4 mm.

In order to determine the bioactivity of anodised wafers, cleaved wafer segments were placed in a simulated body fluid (SBF) solution for a period of time ranging from 2 hours to 6 weeks. The SBF solution was prepared by dissolving reagent grade salts in deionised water. The solution contained ion concentrations similar to those found in human blood plasma. The SBF solution ion concentrations and those of human blood plasma are shown at Table 1. The SBF solution was organically buffered at a pH of 7.30±0.05, equivalent to the physiological pH, with trihydroxymethylaminomethane and hydrochloric acid. The porous wafers were stored in ambient air for at least several months prior to immersion in the SBF solution and were therefore hydrated porous silicon wafers. The porous silicon thus comprised a silicon skeleton coated in a thin native oxide, similar to that formed on bulk silicon as a result of storage in air.

TABLE 1

| Ion | Concentration (mM) | |
|---|---|---|
| | Simulated Body Fluid | Human Plasma |
| $Na^+$ | 142.0 | 142.0 |
| $K^+$ | 5.0 | 5.0 |
| $Mg^{2+}$ | 1.5 | 1.5 |
| $Ca^{2+}$ | 2.5 | 2.5 |
| $HCO_3^-$ | 4.2 | 27.0 |
| $HPO_4^{2-}$ | 1.0 | 1.0 |
| $Cl^-$ | 147.8 | 103.0 |
| $SO_4^{2-}$ | 0.5 | 0.5 |

Cleaved wafer segments having typical dimensions of 0.4×50×20 $mm^3$ were placed in 30 $cm^3$ capacity polyethylene bottles filled with the SBF solution and held at 37°±1° C. by a calibrated water bath.

After a known period of time, the segments were removed from the SBF solution, rinsed in deionised water and allowed to dry in ambient air prior to characterisation. The SBF treated segments were examined using scanning electron microscopy (SEM) and x-ray microanalysis (EDX) on a JEOL 6400F microscope. Secondary ion mass spectrometry was carried out using a Cameca 4F instrument and infrared spectroscopy was performed using a Biorad FTS-40 spectrometer.

After periods of immersion in the SBF solution of 2, 4, and 17 hours, there were negligible apatite deposits on both the porous silicon region 20 and the non-porous bulk silicon region 22.

Figure 2:
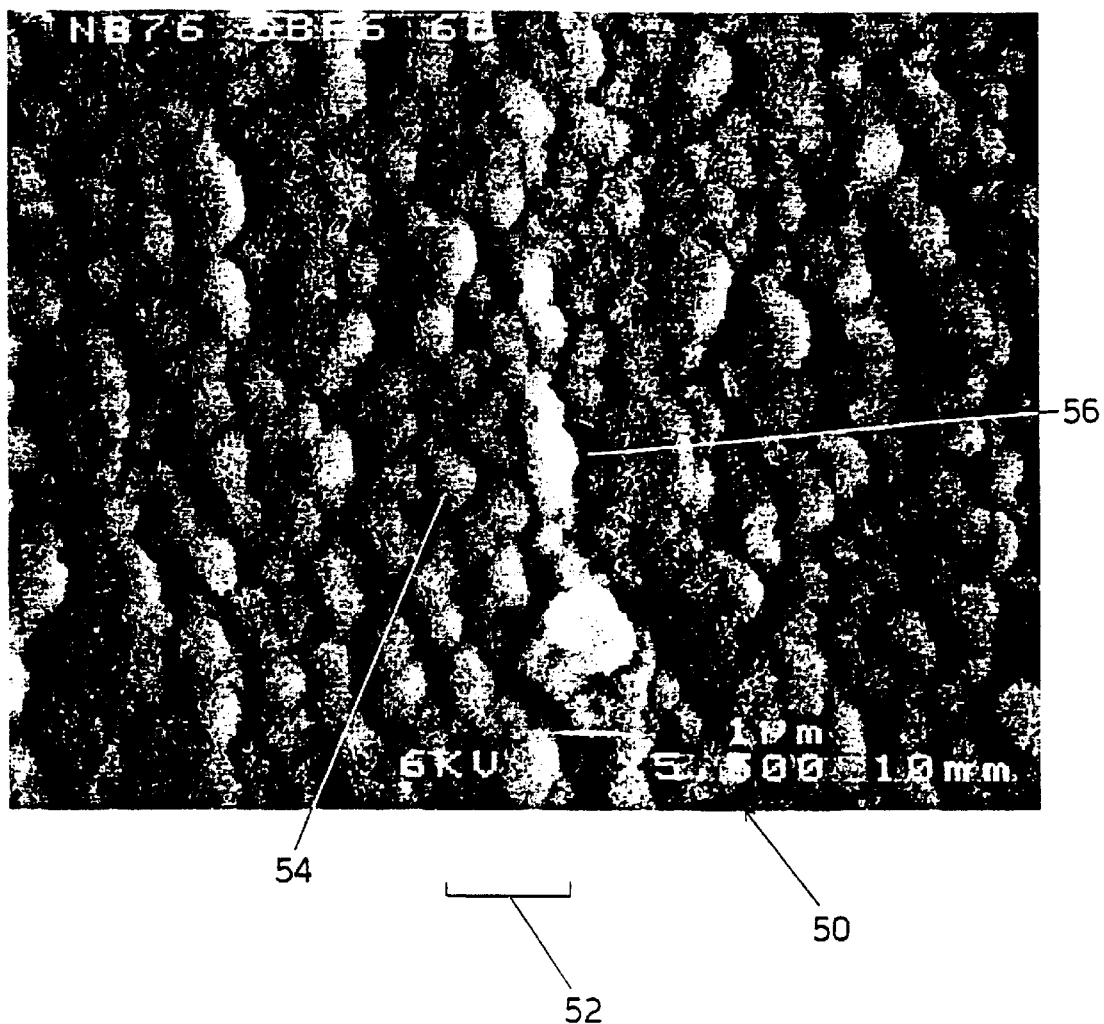
FIG. 2 is a representation of a scanning electron microscope (SEM) micrograph of an apatite deposit on a bulk silicon region adjacent a porous region of the FIG. 1 wafer.

Referring to FIG. 2 there is shown a reproduction of an SEM micrograph indicated generally by 50. The micrograph 50 is an image of part of the region 22 after the wafer 10 had been placed in the SBF solution for a period of 6 days. A scale bar 52 indicates a dimension of 2 µm. The micrograph 50 shows a continuous layer of apatite spherulites 54 covering the surface of the region 22. The apatite spherulites had nucleated at a sufficiently high density to create a relatively smooth film in which boundaries between spherulites such as boundary 56 are indistinct. The film was continuous over an area of at least 100 $µm^2$.

Figure 3:
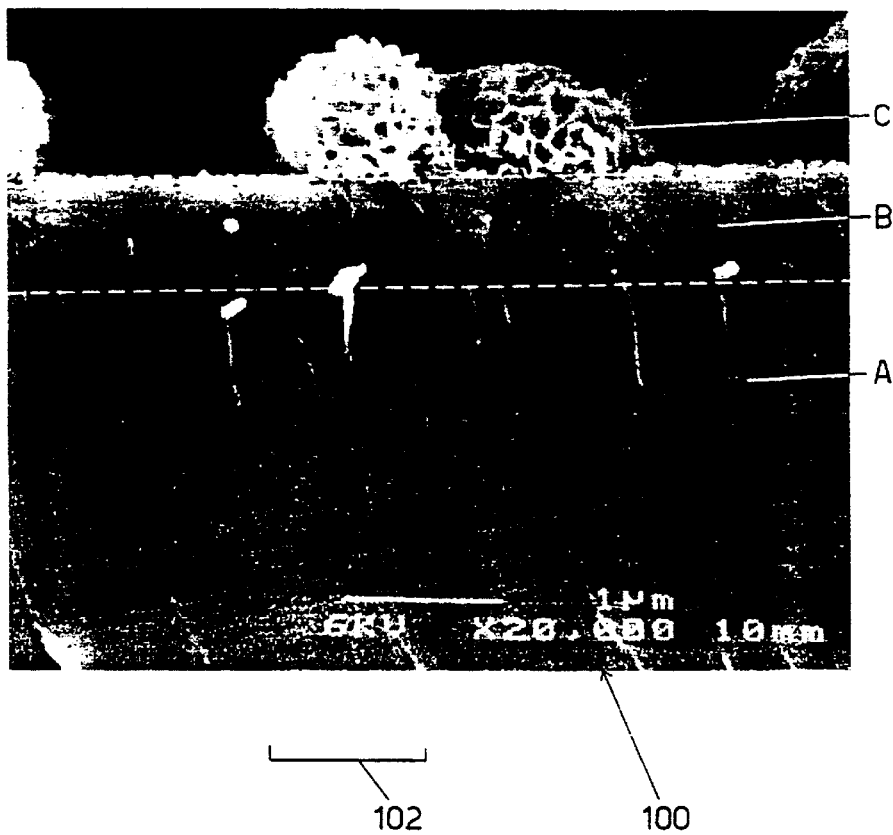
FIG. 3 is a representation of an SEM micrograph of a cross-section of the FIG. 2 silicon region.

Referring to FIG. 3 there is shown a reproduction of an SEM micrograph, indicated generally by 100, of a cross-section of the wafer 10 in the region 22 after the wafer had been immersed in the SBF solution for 6 days. A scale bar 102 indicates a dimension of 1.0 µm. The micrograph 100 indicates three distinct regions, indicated by the letters A, B, and C. EDX analysis confirmed that region A is silicon, corresponding to the original material of the non-porous bulk silicon region 22. Region B exhibited both silicon and oxygen peaks under EDX analysis, indicating that region B comprises silicon oxide. Region C exhibited calcium, phosphorus and oxygen peaks under EDX analysis, consistent with this region comprising spherulites of apatite. The combined SEM and EDX analysis demonstrates that a porous silicon oxide layer (region B) has formed on the bulk silicon (region A), thereby enabling nucleation and coverage with apatite (region C). SEM analysis of the wafer 10 in the area of the porous silicon region 20 after 6 days immersion in the SBF solution indicated a much lower level of apatite coverage compared with the region 22. The porous silicon region 20 contains a high level of mesoporosity. After 10 days immersion in the SBF solution in which significant layer erosion of the porous silicon had occurred, macropores were visible under SEM analysis in the region 20. The combined SEM and EDX analysis demonstrates that, in contrast to the bulk silicon region 22, apatite nucleation can occur directly on the porous silicon region 20 and does not require the formation of an intermediate porous silicon oxide layer. The intentional introduction of very large (greater than 100 μm diameter) macropores may be advantageous in that it may enable vascular tissue to grow within the structure of the porous silicon.

The formation of apatite deposits has also been observed on wafers having porous silicon porosities other than 18%. A microporous wafer having a porous silicon region with a porosity of 31% was fabricated from a 0.03 Ωcm heavily boron doped p-type CZ silicon wafer by anodisation at an anodisation current density of 100 mAcm$^{-2}$ for one minute in 50 wt % HF. The resulting porous silicon region had a thickness of 9.4 μm and a surface area per unit mass of 250 m$^2$g$^{-1}$. The porous silicon wafer was heavily aged prior to immersion in the SBF solution.

Figure 4:
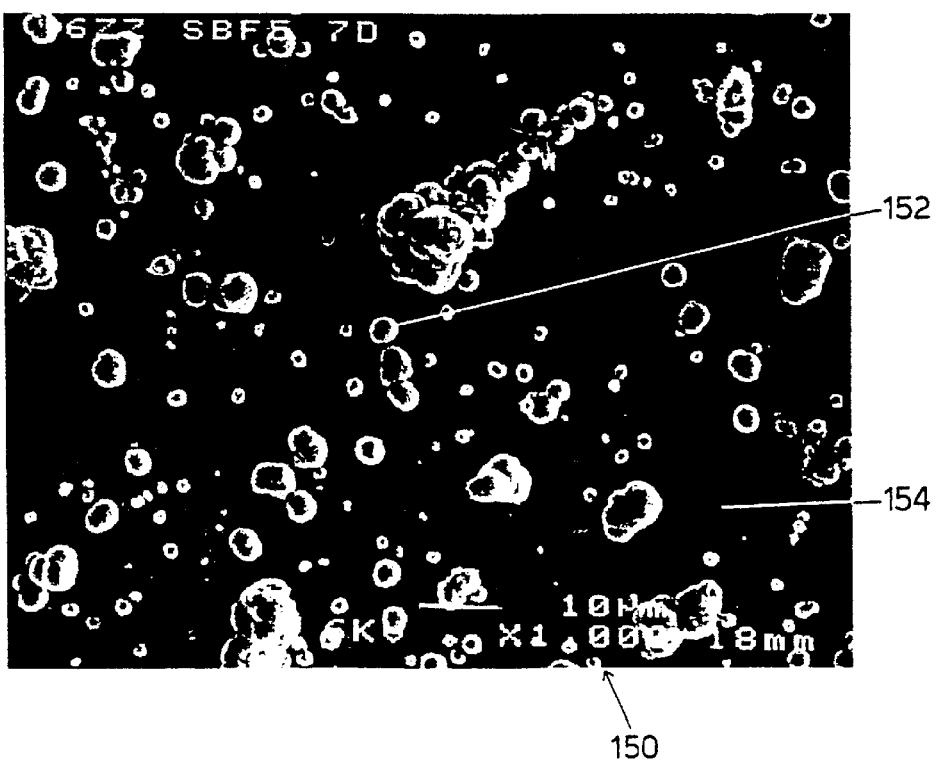
FIG. 4 is a representation of an SEM micrograph showing an apatite spherulite deposited on a porous silicon region of porosity 31%

FIG. 4 shows a representation of an SEM micrograph, indicated generally by 150, of the surface of the 31% porosity porous silicon layer after a segment of the wafer had been immersed in 30 cm$^3$ of the SBF solution for 7 days. The micrograph 150 shows spherulites such as a spherulite 152 of apatite on the surface 154 of the porous silicon.

Microporous wafers having a porous silicon region of a porosity of 48% were fabricated by anodising a lightly boron doped p-type silicon wafer having a resistivity of 30 Ωcm in 50 wt % HF at an anodisation current density of 20 mAcm$^{-2}$ for five minutes. The resulting porous silicon region had a thickness of 6.65 μm and a surface area per unit mass of approximately 800 m$^2$g$^{-1}$. The porous silicon wafer segment was heavily aged prior to immersion in a 150 cm$^3$ polyethylene bottle filled with the SBF solution.

Figure 5A:
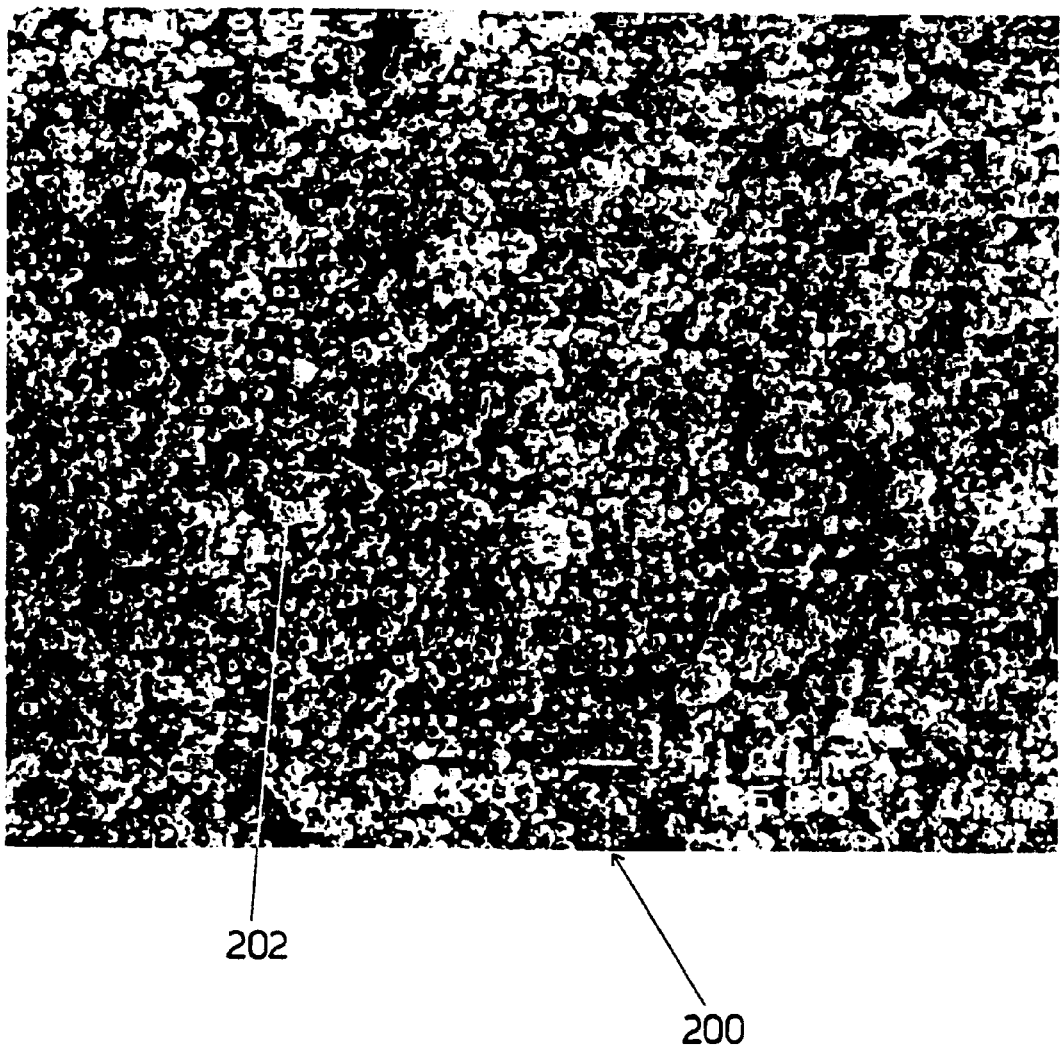
FIG. 5a is a representation of an SEM micrograph of an unanodised region of a silicon wafer anodised to produce a porosity of 48% after immersion in a simulated body fluid solution.
Figure 5B:
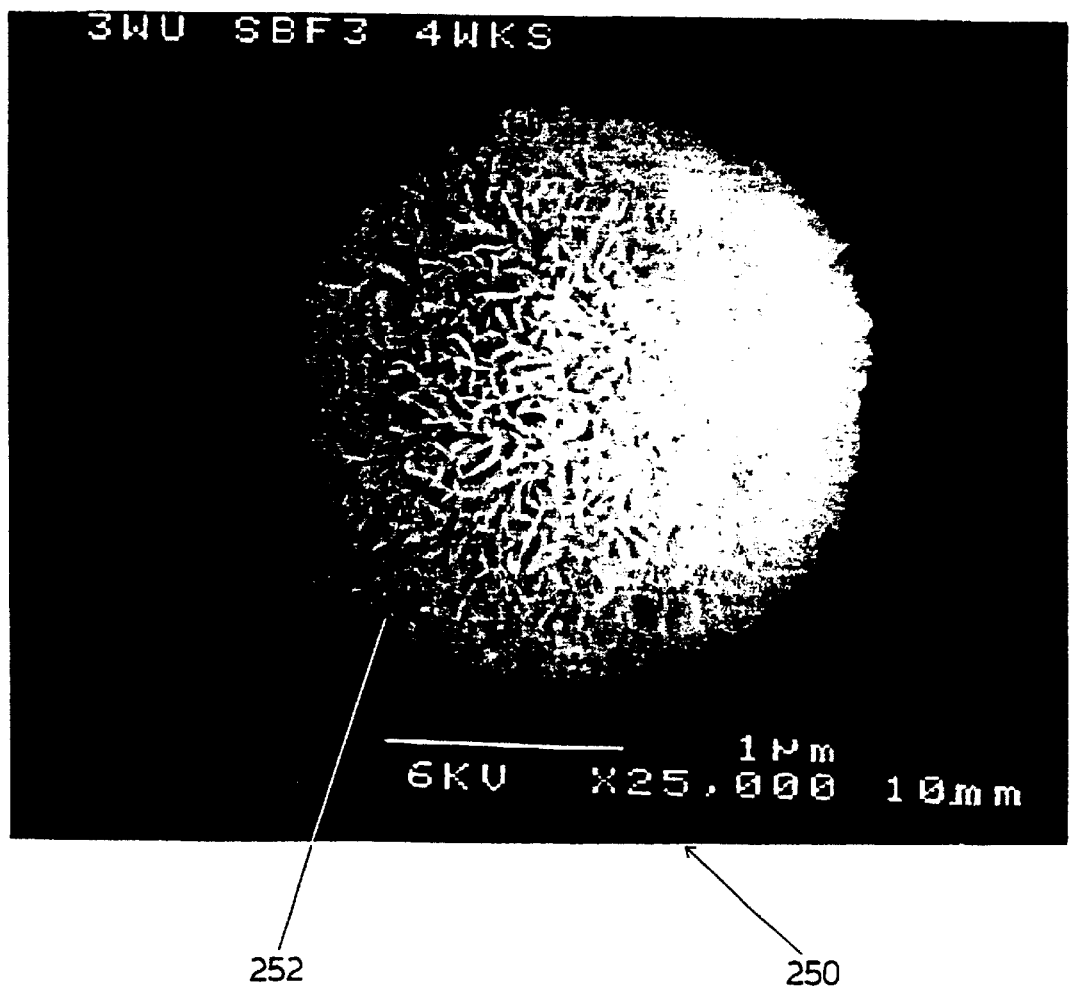
FIG. 5b is a representation of an SEM micrograph of an anodised region of the FIG. 5a wafer.

FIG. 5a shows a representation of a SEM micrograph, indicated generally by 200, of an apatite deposit 202 on an unanodised region of the 48% porosity wafer after a four week immersion period. FIG. 5b shows a representation of a SEM micrograph, indicated generally by 250 of an apatite spherulite 252 deposited on the 48% porosity porous region. The spherulite 252 exhibits a morphology having a columnar structure characteristic of apatite growth on bioactive ceramics as described by P. Li et al. in Journal of Biomedical Materials Research, Volume 28, pages 7–15, 1994. Apatite spherulites having a similar morphology were observed on the unanodised region of the wafer. Cross-sectional EDX spectra of the 48% porosity wafer after immersion in the SBF solution taken across the unanodised region indicated that spherulites contained calcium, phosphorus and oxygen, consistent with apatite. Away from the spherulites, an interfacial layer having a thickness of only 150 nm comprising predominantly silicon and oxygen was observed. Fourier transform infrared spectroscopy confirms the presence of apatite in both the porous and non-porous regions. Both the P–O bending vibrational modes of PO$_4$ tetrahedra at wavenumbers of around 600 cm$^{-1}$ and a broad band around 1400 cm$^{-1}$, attributed to vibrational modes of carbonate groups, were observed.

Some forms of porous silicon are known to be photoluminescent. The observation of red or orange photoluminescence from porous silicon generally indicates the presence of quantum wires or quantum dots of silicon material. Prior to immersion in the SBF solution, the heavily aged 48% porosity wafer exhibited photoluminescence, indicating that despite being hydrated by exposure to ambient air, the porous silicon region maintains a high concentration of quantum wires or dots. The luminescent property was preserved both during and after immersion in the SBF solution. This shows that apatite may be deposited on porous silicon such that the luminescent properties are preserved. Preservation of the luminescent properties after growth of an apatite layer may be a useful property for the development of an electro-optical biosensor.

A wholly mesoporous luminescent porous silicon wafer having a 1 μm thick porous region with a porosity of 70% and a surface area per unit mass of 640 m$^2$ g$^{-1}$ was placed in the SBF solution. After approximately one day the porous region had been completely removed by dissolution in the SBF solution and the wafer was no longer luminescent. No apatite deposits were observed on either the porous silicon region or the non-porous region. It is thought that the mesoporous silicon is wetted more efficiently by the SBF solution and hence the rate of dissolution is higher for mesoporous silicon than microporous silicon. The mesoporous silicon thus shows resorbable biomaterial characteristics. It might be possible to construct a bioactive silicon structure having a limited area of mesoporous silicon to act as a source of soluble silicon. This could produce a locally saturated silicon solution and hence the promotion of apatite deposition.

A macroporous silicon wafer having a porous region of 4% porosity and a thickness of 38 μm behaved like a bulk, unanodised silicon wafer in as much as it did not exhibit growth of an apatite deposit when immersed in the SBF solution for four weeks. In addition, no apatite growth has been observed on a porous silicon region having a porosity of 80% and a thickness of 50 μm which retains its luminescent properties after two weeks immersion in the SBF solution.

As a further control, a cleaved non-porous silicon wafer segment of similar dimensions to the porous silicon wafer segments was placed in 30 cm$^3$ of the SBF solution. An extremely low density of micron size deposits, less than 5000/cm$^2$ was observed after immersion in the SBF solution for five weeks. These deposits were possibly located at surface defects of the silicon wafer. Bulk, non-porous silicon is therefore not bioactive since the rate of growth of apatite deposits is too low for a bond to be formed with living tissue.

These experiments thus indicate that by appropriate control of pore size and porosity, silicon structures can cover virtually the entire bioactivity spectrum. Bulk and purely macroporous silicon are relatively bioinert; high porosity mesoporous silicon is resorbable and microporous silicon of moderate porosity is bioactive.

It is known that changes in chemical composition of biomaterials can also affect whether they are bioinert, resorbable or bioactive. The above experiments were carried out on porous silicon wafers which had not been intentionally doped with any specific elements other than the impurity doping for controlling the semiconductor properties of the silicon.

The elution of calcium from bioactive glass containing SiO$_2$, Na$_2$O, CaO and P$_2$O$_5$ is believed to significantly assist apatite growth by promoting local supersaturation. Calcium has been impregnated into a freshly etched layer of microporous silicon of 55% porosity and having a thickness of 1.2 μm formed in a lightly doped p-type (30 Ωcm) CZ silicon wafer by anodisation at 20 mAcm$^{-2}$ for one minute in 40% aqueous HF. The calcium impregnation was achieved through mild oxidation by storage in a solution containing 5 g of CaCl.2H$_2$O in 125 cm$^3$ pure ethanol for 16 hours. The impregnation of the porous silicon with calcium, sodium or phosphorus or a combination of these species may promote apatite formation on silicon.

The presence of the silicon oxide layer underneath the apatite deposit at the non-porous region adjacent the porous silicon region of the anodised wafers after immersion in the SBF solution indicates that the dissolution of silicon from the porous silicon region may be an important factor for the bioactivity of the porous silicon. The dissolution of the silicon may form a local supersaturated solution which results in the deposition of a porous silicon oxide layer. Apatite is then deposited on the porous silicon oxide. This suggests that a variety of non-porous crystalline, polycrystalline or amorphous silicon based structures containing impregnated calcium and having a higher solubility than normal bulk crystalline silicon in the SBF solution may be bioactive. To significantly assist apatite growth, the level of calcium impregnation needs to be much higher than previously reported calcium doped silicon, though the crystallinity of the silicon need not necessarily be preserved.

Calcium is generally regarded as an unattractive dopant for silicon and consequently there have been few studies of calcium doped silicon. Sigmund in the Journal of the Electrochemical Society, Volume 129, 1982, pages 2809 to 2812, reports that the maximum equilibrium solubility of calcium in monocrystalline silicon is $6.0 \times 10_{18}$ cm$^{-3}$. At this concentration, calcium is unlikely to have any significant effect upon apatite growth. Supersaturated levels of calcium are needed with concentrations in excess of $10^{21}$ cm$^{-3}$ (2 at %). Such very high concentrations may be achieved by:

(a) solution doping of porous silicon as previously described;

(b) ion implantation of porous silicon or bulk silicon with calcium ions; or (c) epitaxial deposition of calcium or calcium compounds followed by thermal treatments.

Figure 6:
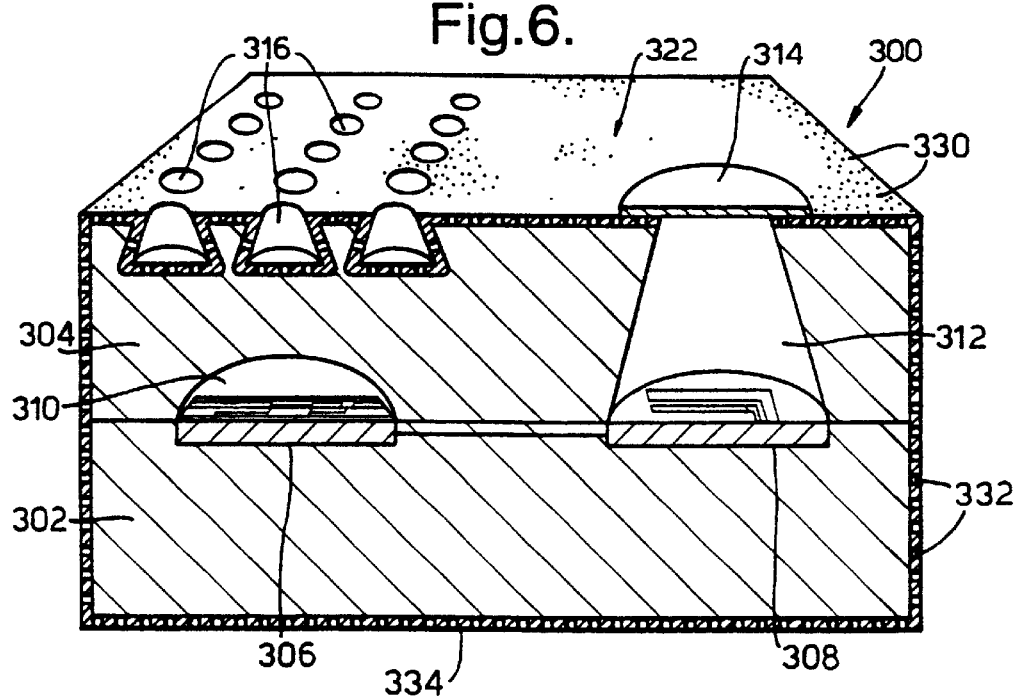
FIG. 6 is a schematic diagram of a biosensor incorporating bioactive silicon.

Referring to FIG. 6 there is shown a schematic diagram of a generalised sensor, indicated generally by 300, for medical applications incorporating bioactive silicon. The sensor 300 comprises two silicon wafer segments 302 and 304. The segment 302 incorporates CMOS circuitry 306 and a sensing element 308 linked to the circuitry 306. The sensing element 308 may be an oxygen sensor, for instance a Clark cell. The CMOS circuitry is powered by a miniaturised battery (not shown) and signals are produced for external monitoring using standard telemetry techniques.

The wafer segment 304 is a micromachined top cover for the segment 302. The segment 304 has two major cavities 310 and 312 machined into it. The cavity 310 has a dome shape. When the segments 302 and 304 are joined together, the cavity 310 is above the CMOS circuitry 306. The cavity 312 is circular in cross-section and extends through the segment 304 to allow the sensing element 308 to monitor the environment surrounding the sensor. The cavity 312 is covered by a permeable membrane 314. In addition to the major cavities 310 and 312, minor cavities, such as cavities 316, are distributed over a top surface 322 of the segment 304. The minor cavities are frusto-conical in shape, with the diameter of its cross-section increasing into the segment. The minor cavities are present to enable the growth of vascular tissue or bone for biological fixation. The cavities 310, 312, and 316 are formed by standard etching techniques, for example ion-beam milling and reactive ion etching through a photoresist mask. At least part of the outer surfaces of the segments 302 and 304 are anodised to form a porous silicon region in order to promote the deposition of apatite and the bonding of the sensor with the tissue. In FIG. 6, the porous silicon is indicated by rings 330 on the top surface of the segment 304 and grooves 332 in the other surfaces. Although FIG. 6 indicates that the outer surfaces of the segments 302 and 304 are covered entirely by porous silicon, it may be sufficient for only the surface 322 and a bottom surface 334 of the segment 302 to incorporate porous silicon. Such an arrangement would be simpler to fabricate. The segments 302 and 304 are bonded together using techniques developed for silicon on insulator technologies. Whilst an anodisation technique has been described for the production of the porous silicon, stain etching techniques are also known for the production of porous silicon. Such techniques may be advantageous for producing porous silicon surfaces on complex shaped structures.

In addition to sensors, bioactive silicon might find applications in electronic prosthetic devices, for example replacement eyes. Other electronic devices which may incorporate bioactive silicon might include intelligent drug delivery systems.

As well as sensors for incorporation into the bodies of humans and other animals, bioactive porous silicon may be used in the fabrication of biosensors for in vitro applications. A composite structure of porous silicon with a layer of apatite thereon may have improved cell compatibility compared with prior art biosensor arrangements. Biosensors are of potentially great importance in the field of in vitro pharmaceutical testing. For automated pharmaceutical testing, a bioasay device might comprise a silicon wafer having a matrix array of porous silicon regions. Cells could then be preferentially located at the porous silicon regions and this would facilitate automated cell analysis after exposure to a pharmaceutical product. The luminescent properties of porous silicon might be utilised to enable an optical cell analysis technique. Workers skilled in the field of biosensors would use their experience to identify which cell cultures were suitable and how the cells' behavior could be monitored.

Whilst the results of in vitro experiments have been described, no in vivo experiments have been described. However, the in vitro experiments are designed to mimic the environment within a human body. From the results of the in vitro experiments it may be concluded that those silicon wafers which produced significant deposits of apatite in the SBF solution would also exhibit bioactive behavior in vivo.

The formation of a film of apatite over a silicon or porous silicon surface in vitro indicates that the bioactive silicon may be to a certain extent a biocompatible form of silicon. The term "biocompabble" does not necessarily indicate that the material is biologically acceptable for all applications but that the material is biologically acceptable for specific applications. Some workers skilled in the field of biocompatibility might regard "tissue compatible" as a more appropriate term to describe this definition of biocompatibility. The layer of apatite may act as a protective barrier reducing the physiological effects of the silicon.

As stated above, mesoporous silicon shows resorbable biomaterial characteristics. From the previously referenced paper by Hench in the Journal of the American Ceramic Society, resorbable biomaterials are materials which are designed to degrade gradually over a period of time and be replaced by the natural host tissue. The characteristics of the mesoporous silicon in the simulated body fluid indicate that mesoporous silicon of an appropriate porosity may be a resorbable biomaterial. As previously discussed the porous region 20 of the bioactive silicon wafer 10 of FIG. 1 contains a high level of mesoporosity. This indicates that controlling the porosity of mesoporous silicon can control whether a porous silicon region is bioactive or resorbable. It may be possible to control the rate at which a porous silicon region is absorbed by tuning the porosity.

Although the dissolution of porous silicon in the SBF solution provides an indication of resorbable biomaterial characteristics, the behavior of a porous silicon region in a living body may be affected by factors which are not reproducible in the SBF solution. If living cells grow on the surface of the porous silicon, these cells may interact with the porous silicon. Thus experiments carried out in the SBF solution do not provide a clear indication of the suitability of a particular form of porous silicon for resorbable material applications. Experiments may have to be carried out in vivo to determine whether a particular desired physiological response is achieved.

Further experiments have been performed which show that it is possible to either enhance or retard the formation of an apatite layer on the porous silicon by the application of a bias current in the SBF solution.

Figure 7:
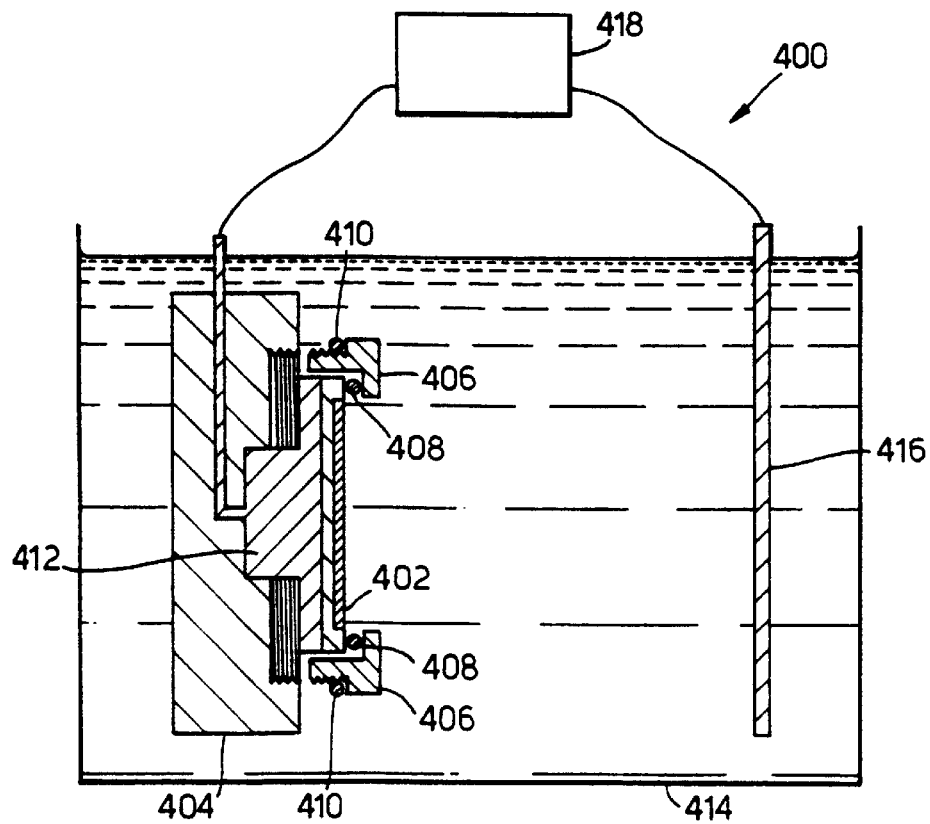
FIG. 7 is a schematic diagram of an electrochemical cell for the electrical control of bioactivity.

Referring to FIG. 7 there is shown a schematic diagram of an electrochemical cell 400 for applying a galvanostatic loading to a whole silicon wafer 402. The wafer 402 is a heavily doped n-type (100) oriented silicon wafer of resistivity 0.012 Ωcm which prior to loading in the cell 400 was anodized in 40 wt % aqueous HF at 100 mA cm$^{-2}$ for one minute to form a bioactive porous silicon layer of approximately 20% porosity having a thickness of 11 $\mu$m with a BET measured surface area of approximately 70 m$^2$g$^{-1}$. After anodisation, the wafers are spun dry in air until their weight has stabilised and then immediately loaded into the cell 400.

The wafer 402 is inserted into a PTFE cassette 404 and mounted using a threaded PTFE ring 406 which is screwed into the cassette 404 and which compress PTFE coated O-rings 408 and 410. In the cassette 404, the silicon wafer is pushed against a metal back plate 412. The plate 412 provides an electrical contact to a rear face of the silicon wafer, and in the cassette an area of 36 cm$^2$ of the front porous face of the silicon wafer is exposed. The cassette 404 is placed in a polycarbonate tank 414, within a waterbath, containing two litres of SBF solution maintained at 37±1° C. with organic buffering at pH=7.3±0.05. A spiral platinum counterelectrode 416 is also inserted into the SBF solution. A d.c. galvanostatic power supply 418 is used to maintain a constant electrical current between the wafer 402 and the counterelectrode 416. The wafer 402 may either be under cathodic or anodic bias control. The power supply 418 provides a constant current of 36 mA, which corresponds to a current density. at the silicon wafer of approximately 1 mA cm$^{-2}$ if current flow is primarily through the silicon skeleton or approximately 1 $\mu$A cm$^{-2}$ if current flow is uniformly distributed across the entire silicon-SBF interface via the pore network of the porous silicon. The current flow is maintained for three hours. After removal from the cell 400, the wafers 402 are rinsed in deionised water and spun dried.

After the three hour SBF exposure, the porous silicon wafer surface was examined in a JEOL 6400F scanning electron microscope (SEM) at an accelerating potential of 6 kV. Porosified wafers which were anodically biased, together with control porosified wafers which received no bias showed no evidence of surface deposits on the porous silicon. The wafer which was cathodically biased however was completely covered with spherulites which had merged to form a continuous layer. Plan view EDX analysis showed that this overlayer is a predominantly calcium and phosphorous containing mineral, with other SBF constituents such as carbon, magnesium, sodium and chlorine being close to EDX detection limits (i.e. <1 atomic %). Plan view EDX analysis of the unbiased and anodically biased wafers showed only the presence of silicon and oxygen.

Cross-sectional SEM and EDX analysis showed that the calcium and phosphorous rich mineral developed under cathodic bias is restricted to the top of the porous silicon layer and is relatively thin, having a thickness of approximately 0.2 $\mu$m. Within the porous silicon the calcium and phosphorous levels are below EDX detection limits for all samples. The porous silicon layer given the anodic loading showed a significant build up of oxygen within the top 0.5 $\mu$m of the layer.

Secondary ion mass spectrometry (SIMS) was utilised to compare the extent and depth to which layers were calcified after the three differing treatments, together with the depth distribution of other specific elements. Freshly etched microporous silicon has been shown to contain very low levels of for example calcium and sodium (present in SBF) but appreciable levels of fluorine (not present in SBF).

Figure 8:
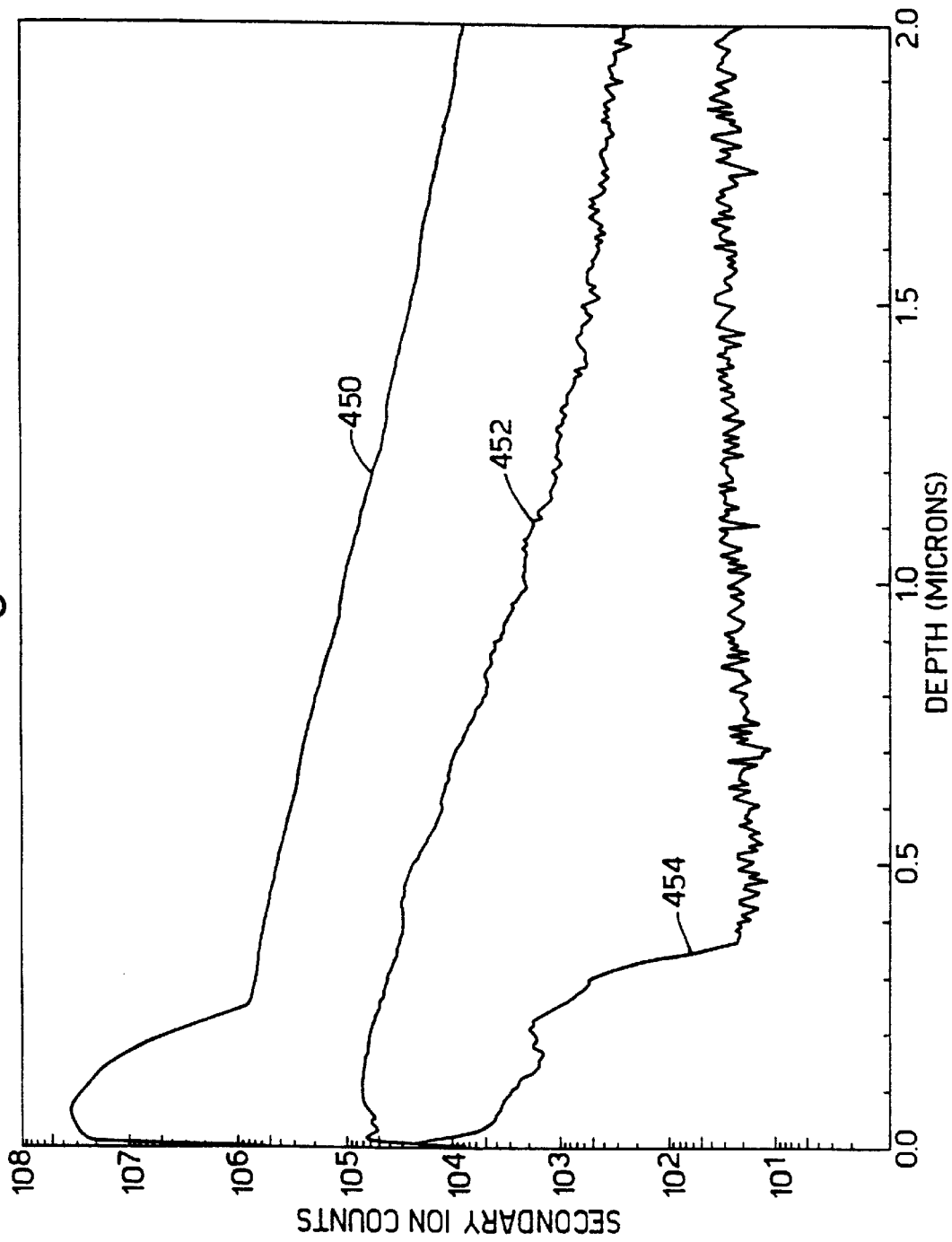
FIG. 8 is a plot of a calcium concentration profile in porous silicon wafers after treatment in the FIG. 7 cell.

FIG. 8 is a SIMS plot shows the varying levels of calcification resulting from the electrical biasing treatments. In FIG. 8, the SIMS plot from a cathodically biased wafer is shown by a line 450, the SIMS plot from an unbiased wafer is shown by line 452, and a SIMS plot from an anodically biased wafer is shown by a line 454. Although deposition has primarily occurred near the surface of the porous silicon, in all cases calcium levels were above the background level throughout the 11 $\mu$A thick layer. The line 450 shows that cathodic biasing has raised the degree of calcification and anodic biasing has lowered it compared with the unbiased wafer. The SIMS measurements also indicated the presence of the SBF constituents throughout the porous silicon layer and that there had been significant movement and loss of fluorine as a result of the cathodic biasing, together with some degree of retention within the overlayer.

It is well established that in vitro and in vivo tissues only respond favorably over quite restricted ranges of input power, current and voltage in electrostimulation experiments. These ranges are sensitive to many factors including the nature of the stimulating electrodes. The biasing experiments described above indicate that the kinetics of the calcification process of porous silicon can be accelerated in vitro and therefore possibly in vivo by the application of a cathodic bias. They also suggest that when dissimilar silicon structures such as porous and bulk silicon are immersed together in physiological electrolytes, galvanic corrosion processes may favour calcification at any cathodic sites that develop.

The potential applications for the bias control of mineral deposition are varied. It is known that the insertion of electrodes into a living organism may result in the formation of a fibrous layer around the electrode, with the thickness of the layer being an indication of the biocompatibility of the electrode. The rapid formation of a stable mineral deposit around microelectrodes in vivo offers potential benefits for the electrostimulation of tissue growth or the stimulation of muscles of paraplegics. The localised control of mineral deposition, where localised regions may be arranged so that a mineral deposit is not formed thereon might have applications in the field of biosensing devices, both in vivo and in vitro. The process of enhanced mineral deposition may be beneficial in the coating of silicon based integrated circuits prior to their implantation in the body.

Whilst the above description of the electrical control of the deposition of a mineral is concerned with the deposition on porous silicon, mineral deposits have also been observed when a cathodic bias is applied to an unanodised wafer in the SBF solution.

In a further embodiment, it has been found that certain types of polycrystalline silicon (polysilicon) are also capable of inducing calcium phosphate deposition from an SBF solution and are hence bioactive.

In order to produce bioactive polycrystalline silicon, 100 mm diameter <100>p-type CZ silicon wafers having a resistivity in the range 5 to 10 Ωcm are coated front and back with a 0.5 $\mu$m thick wet thermal oxide and subsequently a 1 $\mu$m thick polysilicon layer of varying microstructure. The oxide layer is grown in a Thermco TMX9000 diffusion furnace and the polysilicon layer is grown in a Thermco TMX9000 low pressure chemical vapour deposition hot walled furnace. For thermal oxide growth, the furnace tube is held at a uniform temperature of 1000° C., and the wet thermal oxide is grown using steam oxidation for 110 minutes. The subsequent deposition of the polysilicon layer involves the pyrolysis of $SiH_4$ at a pressure in the range 250 to 300 mtorr with the furnace tube held at a temperature in the range 570 to 620° C.

It is well established that the microstructure of the polysilicon layer is sensitive to many deposition parameters such as temperature, pressure, gas flow rate, and substrate type, as described in Chapter 2 of "Polycrystalline Silicon for Integrated Circuit Applications" by T. Kamins, published by Kluwer Acad. Publ. 1988. Polysilicon layers of widely varying microstructure and morphology were obtained by using different deposition temperatures of 570° C., 580° C., 590° C., 600° C., 610° C. and 620° C. Cross-sectional transmission electron microscopy analysis revealed that the layer deposited at 570° C. was virtually amorphous near its surface whereas the layers deposited at 600° C. and 620° C. were polycrystalline throughout their depths. The grain size varies appreciably with deposition temperature and significantly with depth for a given layer.

Cleaved wafer segments having typical dimensions of 0.5×50×20 mm³ were then placed in separate 30 cm³ polyethylene bottles filled with SBF solution as previously described, with the temperature of the SBF maintained at 37° C.±1 C. The different polysilicon layers were observed to have varying levels of stability in the SBF solution as determined by cross-sectional SEM imaging. After 64 hours in the SBF solution, the polysilicon layer deposited at 620° C. was thinned to approximately 60% of its original thickness, whereas the thickness of the layer deposited at 570° C. was substantially unchanged after 160 hours in the SBF solution.

Mineral deposits were observed to nucleate and proliferate over certain of the polysilicon layers. These deposits were observed using plan-view SEM. After two weeks immersion in the SBF solution, mineral deposits were observed on the polysilicon layers deposited at 600° C. and 620° C. but not on the layer deposited at 570° C. These observations indicate that as for the porous silicon there is a reactivity window, dependent on the microstructure, for optimum bioactivity. The greatest density of mineral deposits were observed with the polysilicon layer deposited at 600° C. Significant levels of mineral deposits were observed on both the front and back of the silicon wafers, consistent with there having been polysilicon deposition on both sides.

EDAX analysis of the deposits indicated the presence of calcium, phosphorous and oxygen, consistent with some form of apatite having nucleated. The morphology of the deposits however differs from that of the spherulites previously described in connection with the porous silicon, with the deposits appearing to be more angular. The reasons for this are not understood but could reflect a slightly different local pH at the nucleation sites on the polysilicon. P. Li et al. in Journal of Applied Biomaterials, Volume 4, 1993, page 221, reported that the apatite morphology observed at a pH of 7.3 is significantly different from that observed at a pH of 7.2 for growth on silica gel.

The potential applications for bioactive polysilicon are potentially broader than those for bioactive porous silicon. It is possible to coat a variety of substrates with polysilicon which could not be coated with monocrystalline silicon. Surgical implants could be coated with a layer of polysilicon in order to improve adhesion with bone. Polysilicon is also highly compatible with VLSI technology offering the prospect of complex electronic circuitry being made biocompatible. Polysilicon can be surface micromachined in order to produce a variety of devices and packaging arrangements.

Figure 9:
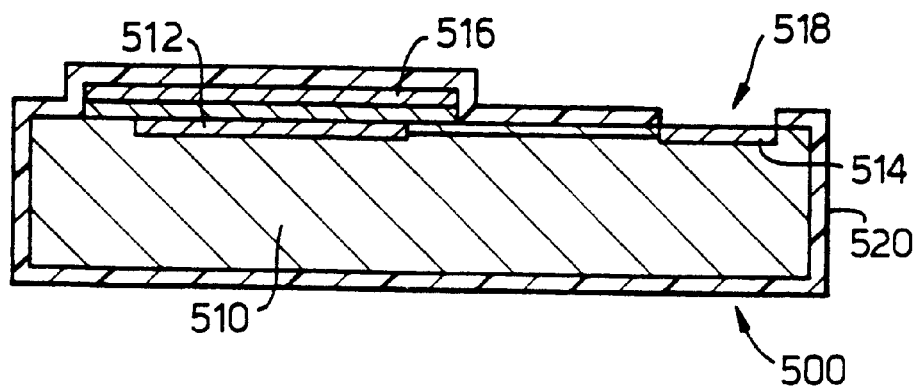
FIG. 9 is a schematic diagram of a biosensor device incorporating bioactive polycrystaliine silicon of the invention.

One possible bioactive silicon packaging concept has already been described with reference to FIG. 6. With bioactive polysilicon, it might be possible to construct smaller biochips. Referring to FIG. 9 there is shown a schematic diagram of a biosensor device 500 incorporating bioactive polysilicon. The device 500 comprises a bulk silicon wafer 510 onto which a CMOS circuit 512 and a sensor element 514 are fabricated. The sensor element 514 is electrically connected to the circuit 512. The circuit 512 is protected by a barrier layer 516 of for example silicon oxide and silicon nitride. The whole of the device 500 except for a window 518 to the sensor element 514 is covered with a layer 520 of bioactive polysilicon. The barrier layer 516 is required because polysilicon itself is not a good protective layer for silicon based circuitry due to diffusion through grain boundaries. The barrier layer 516 is therefore interposed between the circuit 512 and the polysilicon layer 520.

By analogy with the results using porous silicon, the bioactivity of polycrystalline silicon might be improved by doping it with calcium, sodium or phosphorus or a combination of these species.

Bioactive polysilicon might be a suitable substrate for bioassay device applications. L. Bousse et al. in IEEE Engineering in Medicine and Biology, 1994 pages 396 to 401 describe a biosensor for performing in vitro measurements in which cells are trapped in micromachined cavities on a silicon chip. Such an arrangement might beneficially incorporate a composite structure of polysilicon with a layer of apatite thereon, the cells locating themselves preferentially on regions of apatite.

What is claimed is:

1. A composite structure comprising a bioactive silicon region and a mineral deposit thereon.

2. A composite structure according to claim 1, wherein the mineral deposit is apatite.

3. A composite structure according to claim 1 or claim 2, wherein the bioactive silicon region is porous silicon.

4. A composite structure according to claim 1 or claim 2, wherein the bioactive silicon is polycrystalline silicon.

5. A composite structure according to 1 wherein the bioactive silicon comprises silicon selected from the group consisting of porous crystalline silicon, porous amorphous silicon, porous polycrystalline silicon, non-porous crystalline silicon, and non-porous polycrystalline silicon.

6. A method of fabricating a biosensor, wherein the method includes the step of forming a composite structure of bioactive silicon and a mineral deposit thereon.

* * * * *